(12) United States Patent
Choi et al.

(10) Patent No.: US 11,788,154 B2
(45) Date of Patent: Oct. 17, 2023

(54) METHOD FOR IDENTIFYING RACEHORSE USING MICROSATELLITE MARKER

(71) Applicant: Korea Racing Authority, Gwacheon-si (KR)

(72) Inventors: Daeha Choi, Busan (KR); Sunyoung Lee, Seoul (KR); Shinwook Kang, Gwacheon-si (KR); Manbea Hu, Anyang-si (KR); Jundong Yu, Gunpo-si (KR); Hyuncheol Lee, Uiwang-si (KR)

(73) Assignee: Korea Racing Authority, Gwacheon-si (KR)

( * ) Notice: Subject to any disclaimer, the term of this patent is extended or adjusted under 35 U.S.C. 154(b) by 0 days.

(21) Appl. No.: 17/379,258

(22) Filed: Jul. 19, 2021

(65) Prior Publication Data
US 2022/0220567 A1 Jul. 14, 2022

(30) Foreign Application Priority Data
Jan. 8, 2021 (KR) .......................... 10-2021-0002808

(51) Int. Cl.
*C12Q 1/6888* (2018.01)
(52) U.S. Cl.
CPC ..... *C12Q 1/6888* (2013.01); *C12Q 2600/124* (2013.01); *C12Q 2600/156* (2013.01)
(58) Field of Classification Search
None
See application file for complete search history.

(56) References Cited

FOREIGN PATENT DOCUMENTS

| GB | WO 02/092851 A2 * | 11/2002 | ............... C12Q 1/68 |
| KR | 10-2012-0096358 A | 8/2012 | |

OTHER PUBLICATIONS

Dorji (PLOS one, 2018, 13(6): e0199376, pp. 1-11 and supplemental pages ).*
Office Action dated Jul. 20, 2022 in Korean Application No. 10-2021-0002808.
Jigme Dorji et al., "Genetic diversity and population structure of three traditional horse breeds of Bhutan based on 29 DNA microsatellite markers", PLOS ONE, Jun. 27, 2018, vol. 13, No. 6, pp. 1-11 (11 pages total).

* cited by examiner

*Primary Examiner* — Sarae L Bausch
(74) *Attorney, Agent, or Firm* — Sughrue Mion, PLLC

(57) ABSTRACT

Provided is a method for identifying a racehorse including amplifying a target gene by a multiplex PCR using a microsatellite marker obtained by combining one or more sets selected from a first set consisting of AHT4, AHT5, ASB2, HMS3, HMS6, HMS7, HTG4, HTG10, VHL20, ASB17, ASB23, HMS1, LEX3, CA425, HMS2, HTG6, HTG7, LEX033, AMEL, HMS18, LEX27, SRY, and LEX020 and a second set consisting of HTG21, COR089, TKY279, TKY287, TKY294, TKY297, TKY301, TKY312, TKY321, TKY325, TKY333, TKY337, TKY341, TKY343, TKY344, TKY374, and TKY394; detecting alleles in the product amplified in the multiplex PCR amplification step and analyzing the sizes of the alleles using an electrophoresis apparatus to determine a genotype of the racehorse; and summarizing the sizes of the alleles analyzed using the electrophoresis apparatus according to the population and breed of racehorses to plot the number and a frequency distribution of the alleles based on the summarized results.

2 Claims, 9 Drawing Sheets

Specification includes a Sequence Listing.

FIG. 1
| Marker | Peak Electropherograms | Reading |
|---|---|---|
| AHT4 | 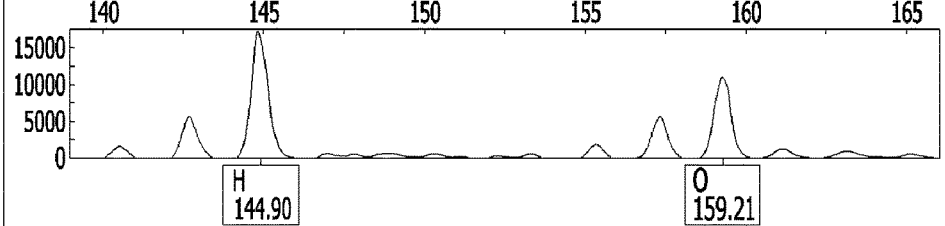 Sample File: 00-Positive.Control(23-Plex) G03 21.fsa — Marker: AHT4<br>H 144.90, O 159.21 | H/O |
| AHT5 | 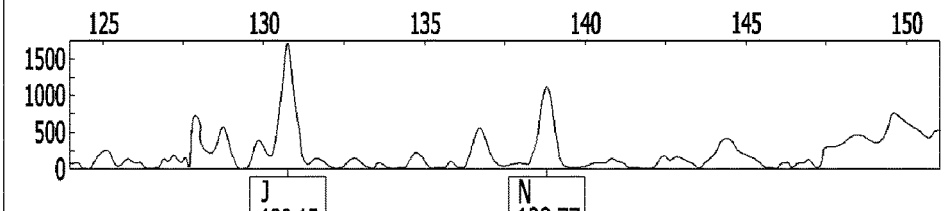 Sample File: 00-Positive.Control(23-Plex) G03 21.fsa — Marker: AHT5<br>J 130.15, N 138.77 | J/N |
| ASB2 | 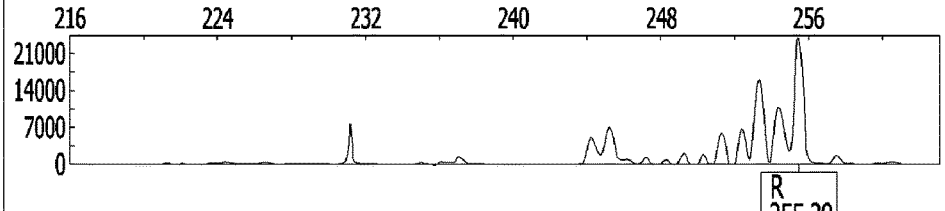 Sample File: 00-Positive.Control(23-Plex) G03 21.fsa — Marker: ASB2<br>R 255.29 | R/R |
| HMS3 | 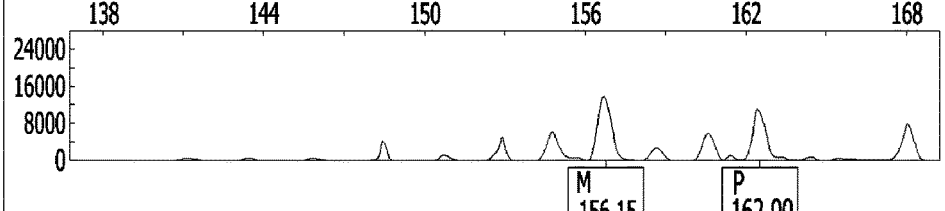 Sample File: 00-Positive.Control(23-Plex) G03 21.fsa — Marker: HMS3<br>M 156.15, P 162.00 | M/P |

FIG. 2

| Marker | Peak Electropherograms | Reading |
|---|---|---|
| HMS6 | Sample File: 00-Positive.Control(23-Plex) G03 21.fsa; Marker: HMS6; K 158.76, P 169.50 | K/P |
| HMS7 | Sample File: 00-Positive.Control(23-Plex) G03 21.fsa; Marker: HMS7; L 177.03, Q 187.48 | L/Q |
| HTG4 | Sample File: 00-Positive.Control(23-Plex) G03 21.fsa; Marker: HTG4; K 127.11, L 129.25 | K/L |
| HTG10 | Sample File: 00-Positive.Control(23-Plex) G03 21.fsa; Marker: HTG10; I 95.17, R 113.59 | I/R |
| VHL20 | Sample File: 00-Positive.Control(23-Plex) G03 21.fsa; Marker: VHL20; M 96.35, N 98.59 | M/N |

FIG. 3

| Marker | Peak Electropherograms | | | Reading |
|---|---|---|---|---|
| ASB17 | Sample File: 00-Positive.Control(23-Plex) G03 21.fsa | Sample File: 00-Positive.Control(23-Plex) | Marker: ASB17 | M/N |
| | Peaks at M 110.31, N 112.27 (range 93–123) | | | |
| ASB23 | Sample File: 00-Positive.Control(23-Plex) G03 21.fsa | Sample File: 00-Positive.Control(23-Plex) | Marker: ASB23 | K/S |
| | Peaks at K 191.54, S 207.82 (range 178.5–213.5) | | | |
| HMS1 | Sample File: 00-Positive.Control(23-Plex) G03 21.fsa | Sample File: 00-Positive.Control(23-Plex) | Marker: HMS1 | I/I |
| | Peak at I 175.94 (range 170–190) | | | |
| LEX3 | Sample File: 00-Positive.Control(23-Plex) G03 21.fsa | Sample File: 00-Positive.Control(23-Plex) | Marker: LEX3 | F/H |
| | Peaks at F 147.64, H 152.46 (range 144–174) | | | |
| CA425 | Sample File: 00-Positive.Control(23-Plex) G03 21.fsa | Sample File: 00-Positive.Control(23-Plex) | Marker: CA425 | O/O |
| | Peak at O 248.84 (range 227.5–252.5) | | | |

FIG. 4

| Marker | Peak Electropherograms | Reading |
|---|---|---|
| HMS2 | Sample File: 00-Positive.Control(23-Plex) G03 21.fsa; Marker: HMS2. Peaks: K 223.37, L 225.27 | K/L |
| HTG6 | Sample File: 00-Positive.Control(23-Plex) G03 21.fsa; Marker: HTG6. Peaks: G 80.85, O 96.82 | G/O |
| HTG7 | Sample File: 00-Positive.Control(23-Plex) G03 21.fsa; Marker: HTG7. Peak: O 126.89 | O/O |
| LEX020 | Sample File: 00-Positive.Control(23-Plex) G03 21.fsa; Marker: LEX020. Peak: 200 200.00 | 200 |
| LEX027 | Sample File: 00-Positive.Control(23-Plex) G03 21.fsa; Marker: LEX027. Peaks: N 193.13, Q 199.26 | N/Q |

FIG. 5

| Marker | Peak Electropherograms | Reading |
|---|---|---|
| LEX033 | Sample File: 00-Positive.Control(23-Plex) G03 21.fsa — Marker: LEX033; peaks L 206.24, M 208.25 | L/M |
| HMS18 | Sample File: 00-Positive.Control(23-Plex) G03 21.fsa — Marker: HMS18; peaks L 169.83, M 171.69 | L/M |
| AMEL | Sample File: 00-Positive.Control(23-Plex) G03 21.fsa — Marker: AMEL; peak X 230.98 | X/X |
| SRY | 19-156314-29-52.fsa — SRY; peak Y 426.89 | X/Y |
| TKY287 | Sample File: 00-Positive.Control(23-Plex) G03 21.fsa — Marker: TKY287; peaks K 220.22, N 226.23 | K/N |

FIG. 6

| Marker | Peak Electropherograms | Reading |
|---|---|---|
| TKY294 | Sample File: 00-Positive.Control(23-Plex) G03 21.fsa — Marker: TKY294; peaks N 222.19, P 226.12 | N/P |
| TKY297 | Sample File: 00-Positive.Control(23-Plex) G03 21.fsa — Marker: TKY297; peak P 237.92 | P/P |
| TKY301 | Sample File: 00-Positive.Control(23-Plex) G03 21.fsa — Marker: TKY301; peaks N 152.33, P 156.22 | N/P |
| TKY312 | Sample File: 00-Positive.Control(23-Plex) G03 21.fsa — Marker: TKY312; peaks I 102.00, Q 118.10 | I/Q |
| TKY325 | Sample File: 00-Positive.Control(23-Plex) G03 21.fsa — Marker: TKY325; peak P 192.01 | P/P |

FIG. 7

| Marker | Peak Electropherograms | Reading |
|---|---|---|
| TKY333 | Sample File: 00-Positive.Control(23-Plex) G03 21.fsa / Marker: TKY333. Peaks: K 90.34, R 103.77 | K/R |
| TKY337 | Sample File: 00-Positive.Control(23-Plex) G03 21.fsa / Marker: TKY337. Peaks: M 174.21, O 178.00 | M/O |
| TKY341 | Sample File: 00-Positive.Control(23-Plex) G03 21.fsa / Marker: TKY341. Peaks: K 141.61, R 155.11 | K/R |
| TKY343 | Sample File: 00-Positive.Control(23-Plex) G03 21.fsa / Marker: TKY343. Peaks: N 155.00, U 168.84 | N/U |
| TKY344 | Sample File: 00-Positive.Control(23-Plex) G03 21.fsa / Marker: TKY344. Peaks: K 91.46, M 95.39 | K/M |

FIG. 8

| Marker | Peak Electropherograms | | | Reading |
|---|---|---|---|---|
| TKY374 | Sample File: 00-Positive.Control(23-Plex) G03 21.fsa | Sample File: 00-Positive.Control(23-Plex) | Marker: TKY374 | M/O |
| TKY394 | Sample File: 00-Positive.Control(23-Plex) G03 21.fsa | Sample File: 00-Positive.Control(23-Plex) | Marker: TKY394 | J/P |
| TKY279 | Sample File: 00-Positive.Control(23-Plex) G03 21.fsa | Sample File: 00-Positive.Control(23-Plex) | Marker: TKY279 | 123/129 |
| TKY321 | Sample File: 00-Positive.Control(23-Plex) G03 21.fsa | Sample File: 00-Positive.Control(23-Plex) | Marker: TKY321 | I/I |
| HTG21 | Sample File: 00-Positive.Control(23-Plex) G03 21.fsa | Sample File: 00-Positive.Control(23-Plex) | Marker: HTG21 | 123/129 |

TKY374 peaks: M 208.87, O 212.59
TKY394 peaks: J 240.64, P 252.17
TKY279 peaks: 123 (122.96), 129 (128.85)
TKY321 peaks: I 183.96
HTG21 peaks: 123 (122.74), 129 (128.63)

METHOD FOR IDENTIFYING RACEHORSE USING MICROSATELLITE MARKER

CROSS-REFERENCE TO RELATED APPLICATION

This application claims priority to and the benefit of Korean Patent Application No. 2021-0002808, filed Jan. 8, 2021, the disclosure of which is incorporated herein by reference in its entirety.

BACKGROUND

1. Field of the Invention

The present invention relates to a method for identifying a racehorse using a microsatellite marker, and more particularly, to a method for identifying a racehorse using a microsatellite marker capable of performing a multiplex polymerase chain reaction (PCR) using a microsatellite marker to more rapidly, accurately and economically distinguish a population of racehorses and stably perform paternity tests, and the like, compared to existing techniques.

2. Discussion of Related Art

In recent years, much interest and effort have been put into the characterization and use of genetic resources as well as attainment, preservation, and management of the genetic resources with the recognized importance of their future value of utility. In particular, the evaluation of molecular biological characterization for understanding the genetic characteristics (such as the origin, variety formation, genetic diversity, taxonomic relationships with other varieties, and the like) of possessed resources using various genetic markers based on DNA polymorphism has been actively performed (Groeneveld et al., (2010) Anim Genet. 41: 6-31).

Microsatellites (MSs) have a structure in which a DNA sequence of 2 to 6 bases is repeated, and is present widely throughout the non-coding regions on eukaryotic DNA (Tautz and Renz, (1984) Nucleic Acids Res. 12: 4127-4138).

Also, there is a lot of polymorphic information because approximately 10 alleles are present per locus of one microsatellite, and DNA extracted from various samples such as blood, hair roots, skin, and the like may be easily amplified due to its small size. In particular, the microsatellites have an advantage in that it is possible to easily analyze allelotypes at low cost because a multiplex PCR technique in which the PCR reaction and amplification may be performed at one time using two or more microsatellite-specific primers is applicable to the microsatellites (Butler, (2007) Biotechniques 43: Sii-Sv).

Such advantages of the microsatellites have been used to analyze the genetic traits and taxonomic relationships of human beings and animals (including domestic animals) since the 1990s, and thus the microsatellites have been used as the most efficient genetic markers (Naidoo and Chetty, (1998) Pathol Oncol Res. 4: 310-315).

To date, the microsatellites have also been used to identify the genetic diversity and quantitative genetic loci of the varieties or groups, distinguish a population of the varieties or groups, and perform paternity tests (Gutierrez-Gil et al., (2010) Meat Sci. 85: 721-729; Costa et al., (2012) BMC Res Notes. 5: 479). In Korea, various academic and industrial outcomes have also been deduced through the analysis of microsatellites, and the development of a method of distinguishing between Korean beef and imported beef, a beef history management system, and the like have been promoted.

Meanwhile, a genetic testing technique using genetic markers (microsatellite markers) developed to conserve the genes of racehorses, study the genetic diversity between varieties, and perform a paternity test has been used, but has drawbacks in that it has its poor utility and accuracy, and it requires relatively high inspection costs and a longer analysis time.

RELATED-ART DOCUMENTS

Patent Documents

Patent Document 01: Korean Patent No. 10-1902508 (registered on Sep. 19, 2018)
Patent Document 02: Korean Patent No. 10-1341813 (registered on Dec. 10, 2013)
Patent Document 03: Korean Patent No. 10-2039309 (registered on Oct. 28, 2019)

SUMMARY OF THE INVENTION

The present invention is directed to providing a method for identifying a racehorse using a microsatellite marker capable of performing a multiplex polymerase chain reaction (Multiplex PCR) using a microsatellite marker to more rapidly, accurately and economically distinguish a population of racehorses and stably perform paternity tests, and the like, compared to existing techniques.

Also, the present invention is directed to providing a method for identifying a racehorse using a microsatellite marker capable of deducing more accurate outcomes at lower costs when compared to conventional markers to reduce a recall rate and minimize inspection time and inspection manpower, and also distinguishing a population of general horses, donkeys, and the like and performing paternity tests, thereby enhancing compatibility.

The technical subjects to be achieved by the present invention are not limited to the aforementioned technical subjects, and other subjects which are not mentioned above will be clearly understood from the following detailed description by those skilled in the art to which the present invention belongs.

One aspect of the present invention provides a method for identifying a racehorse using a microsatellite marker, which includes amplifying a target gene by a multiplex polymerase chain reaction (multiplex PCR) using a microsatellite marker obtained by combining one or more sets selected from a first set consisting of AHT4, AHT5, ASB2, HMS3, HMS6, HMS7, HTG4, HTG10, VHL20, ASB17, ASB23, HMS1, LEX3, CA425, HMS2, HTG6, HTG7, LEX033, AMEL, HMS18, LEX27, SRY, and LEX020 and a second set consisting of HTG21, COR089, TKY279, TKY287, TKY294, TKY297, TKY301, TKY312, TKY321, TKY325, TKY333, TKY337, TKY341, TKY343, TKY344, TKY374, and TKY394; detecting alleles in the product amplified in the multiplex PCR amplification step and analyzing the sizes of the alleles using an electrophoresis apparatus to determine a genotype of the racehorse; and summarizing the sizes of the alleles analyzed using the electrophoresis apparatus according to the population and breed of racehorses to plot the number and a frequency distribution of the alleles based on the summarized results.

In the multiplex PCR amplification step, the microsatellite marker may consist of the first set and the second set.

The first set may include forward and reverse primers consisting of AHT4 (SEQ ID NOs: 1 and 2), AHT5 (SEQ ID NOs: 3 and 4), ASB2 (SEQ ID NOs: 5 and 6), HMS3 (SEQ ID NOs: 7 and 8), HMS6 (SEQ ID NOs: 9 and 10), HMS7 (SEQ ID NOs: 11 and 12), HTG4 (SEQ ID NOs: 13 and 14), HTG10 (SEQ ID NOs: 15 and 16), VHL20 (SEQ ID NOs: 17 and 18), ASB17 (SEQ ID NOs: 19 and 20), ASB23 (SEQ ID NOs: 21 and 22), HMS1 (SEQ ID NOs: 23 and 24), LEX3 (SEQ ID NOs: 25 and 26), CA425 (SEQ ID NOs: 27 and 28), HMS2 (SEQ ID NOs: 29 and 30), HTG6 (SEQ ID NOs: 31 and 32), HTG7 (SEQ ID NOs: 33 and 34), LEX033 (SEQ ID NOs: 35 and 36), AMEL (SEQ ID NOs: 37 and 38), HMS18 (SEQ ID NOs: 39 and 40), LEX27 (SEQ ID NOs: 41 and 42), SRY (SEQ ID NOs: 43 and 44), and LEX020 (SEQ ID NOs: 45 and 46).

The second set may include forward and reverse primers consisting of HTG21 (SEQ ID NOs: 47 and 48), COR089 (SEQ ID NOs: 49 and 50), TKY279 (SEQ ID NOs: 51 and 52), TKY287 (SEQ ID NOs: 53 and 54), TKY294 (SEQ ID NOs: 55 and 56), TKY297 (SEQ ID NOs: 57 and 58), TKY301 (SEQ ID NOs: 59 and 60), TKY312 (SEQ ID NOs: 61 and 62), TKY321 (SEQ ID NOs: 63 and 64), TKY325 (SEQ ID NOs: 65 and 66), TKY333 (SEQ ID NOs: 67 and 68), TKY337 (SEQ ID NOs: 69 and 70), TKY341 (SEQ ID NOs: 71 and 72), TKY343 (SEQ ID NOs: 73 and 74), TKY344 (SEQ ID NOs: 75 and 76), TKY374 (SEQ ID NOs: 77 and 78), and TKY394 (SEQ ID NOs: 79 and 80).

In the multiplex PCR amplification step, the multiplex PCR amplification conditions may include maintenance at 95° C. for 2 minutes, followed by repeating 33 cycles of denaturation at 95° C. for 30 seconds, annealing at 56.5° C. for 90 seconds and extension at 72° C. for 60 seconds, and the final extension at 72° C. for 30 minutes and maintenance at 4° C.

The specific contents of the other embodiments fall within the detailed description of the present invention.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIGS. 1 to 9 are graphs illustrating the racehorse gene (DNA) reading results obtained by a method for identifying a racehorse using a microsatellite marker according to the present invention.

DETAILED DESCRIPTION OF EXEMPLARY EMBODIMENTS

Figure 9:
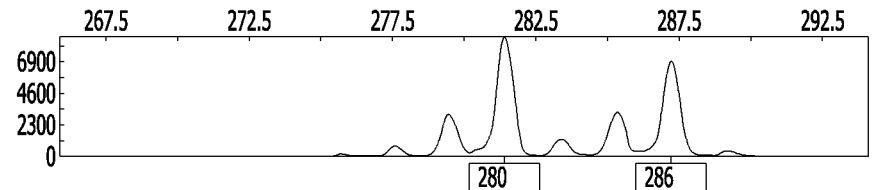

Advantages and features of the present invention and methods for achieving them will be made clear from the embodiments described below in detail with reference to the accompanying drawings. However, it should be understood that the present invention may be embodied in many different forms and may not be construed as being limited to the embodiments set forth herein. Rather, the embodiments disclosed herein are provided so that this disclosure will be thorough and complete and will fully convey the scope of the present invention to those of ordinary skill in the art.

The terminology used herein is for the purpose of describing particular embodiments only and is not intended to be limiting of exemplary embodiments. The singular forms "a," "an" and "the" are intended to include the plural forms as well, unless the context clearly indicates otherwise.

Unless otherwise defined, all the terms including technical and scientific terms used herein have the same meaning as commonly understood by one of ordinary skill in the art to which the present invention pertains. Furthermore, generally used terms defined in most dictionaries are interpreted to have a meaning corresponding to the meaning in the context of the related art, but are not interpreted in an ideal or excessively formal manner unless otherwise defined.

Hereinafter, a method for identifying a racehorse using a microsatellite marker according to the present invention will be described in detail with reference to preferred embodiments thereof.

Meanwhile, the case of the method for identifying a racehorse using a microsatellite marker according to the present invention, which may be used to perform a multiplex polymerase chain reaction (multiplex PCR) using a microsatellite marker to distinguish a population of racehorses or perform paternity tests, is described as one example. However, it should be understood that the technical idea of the present invention is not limited to racehorses as described above, and is also applied to different types of animals including general horses, donkeys, and the like in addition to the racehorses.

In the present invention, the term "microsatellite" refers to a short tandem repeat (STR) having structure in which a DNA sequence of 2 to 6 bases is repeated. Such microsatellites are known to be uniformly distributed in most eukaryotic genomes. In particular, the microsatellites are mainly present in non-coding DNA.

In the present invention, the term "microsatellite marker" refers to a polymorphism that occurs due to a variation in the repeat copies of the microsatellite repeats.

Such a microsatellite marker has various repeat copies of the microsatellite repeats according to the population and species. Therefore, a genetically unique sequence in base pairs present in both ends of a repeated region of a microsatellite may be designed as a primer sequence, and may be subjected to PCR amplification. Then, the sizes of the resulting PCR products may be compared to distinguish the population or species.

In the present invention, the term "primer" refers to a nucleic acid sequence that has a short free 3'-terminal hydroxyl group, that is, a short nucleic acid sequence that may form base pairs with a complementary template and functions as an initiation point for duplication of template strands.

In the present invention, the term "polymerase chain reaction (PCR)" refers to a molecular biological technique that is used to replicate and amplify a desired region of DNA. Specifically, the PCR includes a series of three steps. The first step of PCR is to denature DNA and separate two DNA strands by heating. Each of the separated DNA strands serves as a template.

The second step of PCR is to anneal the DNA strands. In this step, primers for a microsatellite marker bind to the template DNA. The annealing temperature is an important factor that determines the accuracy of the reaction. In this case, when the temperature is too high, a very small amount of the amplified DNA product may be obtained because the primers are very weakly bound to the template DNA. On the other hand, when the temperature is too low, unwanted DNA may be amplified because the primers are non-specifically bound to the template. Therefore, the annealing temperature should be properly adjusted according to the type of the primers used, and the like.

The third step of PCR is an extension step. In this step, when the primers are bound to the template, a heat-resistant DNA polymerase forms new DNA from the template DNA.

When the analysis is performed on several microsatellite markers as in the present invention, multiplex PCR may be used.

In the present invention, the term "multiplex PCR" refers to a PCR technique that amplifies a variety of genes at the same time unlike single PCR that amplifies one gene on one template DNA. In the multiplex PCR, various primer pairs are included in a single PCR mix. In this case, different DNA sequences have a specific range of sizes of amplified product. Therefore, it is desirable that the sizes of the DNA sequences do not overlap each other.

In the multiplex PCR technique, inhibition between the primers may occur because various types of different primer pairs are put into one tube and reacted. Therefore, it is important to select primers for a gene to be amplified when the primers are applied to the multiplex PCR.

Also, the annealing temperature may vary depending on the various primers included in the PCR reaction. Therefore, when PCR primer pairs are applied to the multiplex PCR, it is necessary to optimize the annealing temperature suitable for multiplex PCR so that all of the PCR primer pairs included in the single PCR reaction can effectively bind to the template DNA.

After the PCR is performed as described above, the PCR-amplified products may be identified using a technique capable of classifying the PCR-amplified products depending on the size of the PCR-amplified products, such as SDS-PAGE or capillary electrophoresis.

Specifically, the PCR-amplified products may be subjected to an electrophoresis method, and the like so that the PCR-amplified products can classified according to the size of the PCR-amplified products. Based on the results of size determination, it may be determined how many repeats are included in each allele. Therefore, the populations may be identified by separately constructing a database in which the data on such genotypes and the data of the verified racehorse are recorded or using the established information to compare the data obtained by experiments with such information.

According to the present invention, the microsatellite markers selected as a genetic identification method using a multiplex polymerase chain reaction (multiplex PCR) for identifying genes of a racehorse may be selected based on the microsatellite markers of racehorses reported in the database of the International Society for Animal Genetics (ISAG). Ultimately, a total of 40 microsatellite markers may be divided into two sets in consideration of specific selection conditions such as allele frequency, the annealing temperature of primers, the size of the amplified product, a fluorescent material (a dye), and the like, and then combined to perform a multiplex polymerase chain reaction (multiplex PCR).

In the present invention, the microsatellite markers may be divided into two sets, for example, a first set and a second set. In this case, the first set may be amplified using forward and reverse primers consisting of AHT4 (SEQ ID NOs: 1 and 2), AHT5 (SEQ ID NOs: 3 and 4), ASB2 (SEQ ID NOs: 5 and 6), HMS3 (SEQ ID NOs: 7 and 8), HMS6 (SEQ ID NOs: 9 and 10), HMS7 (SEQ ID NOs: 11 and 12), HTG4 (SEQ ID NOs: 13 and 14), HTG10 (SEQ ID NOs: 15 and 16), VHL20 (SEQ ID NOs: 17 and 18), ASB17 (SEQ ID NOs: 19 and 20), ASB23 (SEQ ID NOs: 21 and 22), HMS1 (SEQ ID NOs: 23 and 24), LEX3 (SEQ ID NOs: 25 and 26), CA425 (SEQ ID NOs: 27 and 28), HMS2 (SEQ ID NOs: 29 and 30), HTG6 (SEQ ID NOs: 31 and 32), HTG7 (SEQ ID NOs: 33 and 34), LEX033 (SEQ ID NOs: 35 and 36), AMEL (SEQ ID NOs: 37 and 38), HMS18 (SEQ ID NOs: 39 and 40), LEX27 (SEQ ID NOs: 41 and 42), SRY (SEQ ID NOs: 43 and 44), and LEX020 (SEQ ID NOs: 45 and 46).

Also, the second set may be amplified using forward and reverse primers consisting of HTG21 (SEQ ID NOs: 47 and 48), COR089 (SEQ ID NOs: 49 and 50), TKY279 (SEQ ID NOs: 51 and 52), TKY287 (SEQ ID NOs: 53 and 54), TKY294 (SEQ ID NOs: 55 and 56), TKY297 (SEQ ID NOs: 57 and 58), TKY301 (SEQ ID NOs: 59 and 60), TKY312 (SEQ ID NOs: 61 and 62), TKY321 (SEQ ID NOs: 63 and 64), TKY325 (SEQ ID NOs: 65 and 66), TKY333 (SEQ ID NOs: 67 and 68), TKY337 (SEQ ID NOs: 69 and 70), TKY341 (SEQ ID NOs: 71 and 72), TKY343 (SEQ ID NOs: 73 and 74), TKY344 (SEQ ID NOs: 75 and 76), TKY374 (SEQ ID NOs: 77 and 78), and TKY394 (SEQ ID NOs: 79 and 80).

Further, the method for identifying a racehorse using a microsatellite marker according to the present invention includes amplifying a target gene by a multiplex polymerase chain reaction (multiplex PCR) using a microsatellite marker obtained by combining one or more sets selected from a first set consisting of AHT4, AHT5, ASB2, HMS3, HMS6, HMS7, HTG4, HTG10, VHL20, ASB17, ASB23, HMS1, LEX3, CA425, HMS2, HTG6, HTG7, LEX033, AMEL, HMS18, LEX27, SRY, and LEX020 and a second set consisting of HTG21, COR089, TKY279, TKY287, TKY294, TKY297, TKY301, TKY312, TKY321, TKY325, TKY333, TKY337, TKY341, TKY343, TKY344, TKY374, and TKY394; detecting alleles in the product amplified in the multiplex PCR amplification step and analyzing the sizes of the alleles using an electrophoresis apparatus to determine a genotype of the racehorse; and summarizing the sizes of the alleles analyzed using the electrophoresis apparatus according to the population and breed of racehorses to plot the number and a frequency distribution of the alleles based on the summarized results.

In the multiplex PCR amplification step, a reagent for the microsatellite marker may consist of 25 μL of a Platinum Multiplex PCR Master mix, 5 μL of a GC enhancer, 10 μL of a primer mix, 4 μL of genomic DNA, and 6 μL of deionized water 6.

In the multiplex PCR amplification step, the reagent for the microsatellite marker may also consist of 12.5 μL of a Platinum Multiplex PCR Master mix, 2.5 μL of a GC enhancer, 5 μL of a primer mix, 2 μL of genomic DNA, and 3 μL of deionized water.

Also, the multiplex PCR amplification conditions in the multiplex PCR amplification step may include maintenance at 95° C. for 2 minutes, followed by repeating 33 cycles of denaturation at 95° C. for 30 seconds, annealing at 56.5° C. for 90 seconds and extension at 72° C. for 60 seconds, and the final extension at 72° C. for 30 minutes and final maintenance at 4° C.

Hereinafter, the method for identifying a racehorse using a microsatellite marker according to the present invention will be described in further detail with reference to the accompanying drawings.

EXAMPLES

1: Selection of Microsatellite Marker for Identifying Racehorse

To select a microsatellite marker which is able to be effectively used to identify a racehorse, microsatellite markers were selected based on the microsatellite markers of the racehorses reported in a database. That is, a total of 40 microsatellite markers were finally selected and divided into two sets in consideration of the specific selection conditions such as allele frequency, the annealing temperature of primers, the size of the amplified product, a fluorescent material (a dye), and the like.

The microsatellite markers are as follows.

That is, the microsatellite markers were selected as two sets such as a first set and a second set. In this case, the first set may be amplified using forward and reverse primers consisting of AHT4 (SEQ ID NOs: 1 and 2), AHT5 (SEQ ID NOs: 3 and 4), ASB2 (SEQ ID NOs: 5 and 6), HMS3 (SEQ ID NOs: 7 and 8), HMS6 (SEQ ID NOs: 9 and 10), HMS7 (SEQ ID NOs: 11 and 12), HTG4 (SEQ ID NOs: 13 and 14), HTG10 (SEQ ID NOs: 15 and 16), VHL20 (SEQ ID NOs: 17 and 18), ASB17 (SEQ ID NOs: 19 and 20), ASB23 (SEQ ID NOs: 21 and 22), HMS1 (SEQ ID NOs: 23 and 24), LEX3 (SEQ ID NOs: 25 and 26), CA425 (SEQ ID NOs: 27 and 28), HMS2 (SEQ ID NOs: 29 and 30), HTG6 (SEQ ID NOs: 31 and 32), HTG7 (SEQ ID NOs: 33 and 34), LEX033 (SEQ ID NOs: 35 and 36), AMEL (SEQ ID NOs: 37 and 38), HMS18 (SEQ ID NOs: 39 and 40), LEX27 (SEQ ID NOs: 41 and 42), SRY (SEQ ID NOs: 43 and 44), and LEX020 (SEQ ID NOs: 45 and 46).

Also, the second set may be amplified using forward and reverse primers consisting of HTG21 (SEQ ID NOs: 47 and 48), COR089 (SEQ ID NOs: 49 and 50), TKY279 (SEQ ID NOs: 51 and 52), TKY287 (SEQ ID NOs: 53 and 54), TKY294 (SEQ ID NOs: 55 and 56), TKY297 (SEQ ID NOs: 57 and 58), TKY301 (SEQ ID NOs: 59 and 60), TKY312 (SEQ ID NOs: 61 and 62), TKY321 (SEQ ID NOs: 63 and 64), TKY325 (SEQ ID NOs: 65 and 66), TKY333 (SEQ ID NOs: 67 and 68), TKY337 (SEQ ID NOs: 69 and 70), TKY341 (SEQ ID NOs: 71 and 72), TKY343 (SEQ ID NOs: 73 and 74), TKY344 (SEQ ID NOs: 75 and 76), TKY374 (SEQ ID NOs: 77 and 78), and TKY394 (SEQ ID NOs: 79 and 80).

2: Analytical Equipment

An analytical apparatus and an auxiliary apparatus as shown in [Table 1] below were used as the analytical equipment.

TABLE 1

| Item | Equipment Name | Model Name (Manufacturer) |
|---|---|---|
| Analytical Apparatus | DNA Auto Analyzer | ABI3130xL (Applied Biosystems) ABI3500xL (Applied Biosystems) |
| Analytical Equipment | DNA Auto Extractor | MFX-6100 (Toyobo) |
|  | DNA Amplifier (PCR) | ABI 9700, Veriti (Applied Biosystems) |

3: Conditions for Analytical Equipment

This experiment was performed under the conditions for analytical equipment as shown in [Table 2] below.

TABLE 2

| Items | Parameters | Conditions |
|---|---|---|
| 1 | Application Type | Fragment |
| 2 | Capillary Length (cm) | 36 |
| 3 | Polymer Type | POP7 |
| 4 | Oven Temperature (° C.) | 60 |
| 5 | Run Voltage (kVolts) | 15 |
| 6 | PreRun Voltage (kVolts) | 18 |
| 7 | Injection Voltage (kVolts) | 1.2 |

4: Analysis Software

3130 Data collection version 3.0: 3130xL Instrument Inspection and Running

3500 Data collection version 3.0: 3500xL Instrument Inspection and Running

GeneMapper version 4.0): 3130xL Result Analysis

GeneMapper version 5.0: 3500xL Result Analysis

5: Analytical Reagents and Compositions

As the first set, the analytical reagents and compositions as listed in [Table 3] below were used.

TABLE 3

| Items | Reagent Name | Single dose |
|---|---|---|
| DNA Extraction | Genomic DNA Purification Kit [MagExtractor (Toyobo)] | |
|  | Lysis & Binding Solution | 8 mL |
|  | Washing Solution | 14 mL |
|  | Magnetic Beads | 1.4 mL |
|  | Proteinase K | 20 μL |
|  | Ethanol | 15 mL |
|  | Elution Solution (Sterilized Water) | 1.4 mL |
| DNA Amplification | Platinum Multiplex PCR Master Mix [Multiplex Kit (Thermo Scientific) used] | |
|  | Platinum Multiplex PCR Master Mix | 25 μL |
|  | GC Enhancer | 5 μL |
|  | Deionized Water | 6 μL |
|  | Primer Mix (Developed by Applicant) | 10 μL |
|  | Genomic DNA (Analysis Sample) | 4 μL |
| DNA Analysis | Hi-Di Formamide | 20 μL |
|  | GeneScan-500 LIZ Size Standard | 0.5 μL |
|  | * Matrix Conditions | |
|  | Filter Set: G5 | 10 μL |
|  | Dye Primer Matrix Standard Set: DS-33 Dye(ABI used) | (Hi-Di 190 μL) |

Meanwhile, in the case of the second set, the analytical reagents and compositions as listed in [Table 3] above were used for DNA extraction and DNA amplification, but the GeneScan 400HD ROX Size standard was used instead of the GeneScan 500LIZ Size standard for DNA analysis.

That is, Filter Set: D, Dye Primer Matrix standard set: DS-30, and the reagents were used in the same amounts.

(1) Platinum Multiplex PCR MasterMix Gene Test Kit

A known product as shown in [Table 4] below was used as the Platinum Multiplex PCR MasterMix gene test kit shown in [Table 3] above.

TABLE 4

| Reagent (50 Reactions) | Volume |
|---|---|
| Platinum Multiplex PCR Master Mix | 1.25 mL × 1 ea (2X) |
| GC Enhancer | 0.3 mL × 1 ea |

(2) Detailed Composition of Reagents for Microsatellite Marker

A reagent for a microsatellite marker blended as shown in [Table 5] below was used as a composition of reagents for DNA amplification as shown in [Table 3] above.

TABLE 5

| Components | Volume (μL)/1 Sample |
| --- | --- |
| Platinum Multiplex PCR Master Mix | 25.0 |
| GC Enhancer | 5.0 |
| Primer Mix | 10.0 |
| Genomic DNA | 4.0 |
| Deionized Water | 6.0 |
| Total Volume | 50.0 |

6: PCR Conditions

This experiment was performed under the PCR conditions as shown in [Table 6] below.

TABLE 6

| Time and Temperature | | | | | |
| --- | --- | --- | --- | --- | --- |
| Initial Step | 33 Cycles | | | Final Extension | Final |
| (1 Cycle) | Denature | Anneal | Extend | (1 Cycle) | Step |
| 95° C. 2 min | 95° C. 30 sec | 56.5° C. 90 sec | 72° C. 60 sec | 72° C. 30 min | 4° C. Hold |

7: PCR Pretreatment Conditions

This experiment was performed under the PCR pretreatment conditions as shown in [Table 7] below.

TABLE 7

| Components | Volume (μL)/1 Sample |
| --- | --- |
| Hi-Di Formamide | 20.0 |
| Size Standard 500LIZ | 0.5 |
| Total Volume | 21 |

8: Dilution Conditions

PCR Products: The PCR products were diluted with deionized water (D.W) at a weight ratio of 1:20, and used in this experiment.

9: Results

The racehorse gene (DNA) reading results as shown in FIGS. 1 to 9 were obtained.

FIGS. 1 to 9 are graphs illustrating the racehorse gene (DNA) reading results obtained by the method for identifying a racehorse using a microsatellite marker according to the present invention.

Referring to FIGS. 1 to 9, it can be seen that the method for identifying a racehorse using a microsatellite marker according to the present invention was able to be used to easily and accurately identify a racehorse.

The method for identifying a racehorse using a microsatellite marker according to the present invention can perform a multiplex polymerase chain reaction (Multiplex PCR) using a microsatellite marker to more rapidly, accurately and economically distinguish a population of racehorses and stably perform paternity tests, and the like, compared to existing techniques.

Also, the method for identifying a racehorse using a microsatellite marker according to the present invention can deduce more accurate outcomes at lower costs when compared to conventional markers to reduce a recall rate and minimize the inspection time and inspection manpower, and can also distinguish a population of general horses, donkeys, and the like and perform paternity tests, thereby enhancing compatibility.

It should be understood that embodiments of the technical idea of the present invention may provide various effects which are not specifically mentioned herein.

While the invention has been shown and described with reference to certain exemplary embodiments thereof, it will be understood by those skilled in the art that various changes in form and details may be made therein without departing from the spirit and scope of the invention as defined by the appended claims. Therefore, it should be understood that the embodiments disclosed herein are only for illustrative purposes and are not intended to be limitative for all aspects.

What is claimed is:

1. A method of genotyping a racehorse, comprising: obtaining a biological sample from the racehorse, amplifying the sample by a multiplex polymerase chain reaction (multiplex PCR) using primers for microsatellite markers comprising a first primer set consisting of a primer pair for AHT4 comprising a forward primer of SEQ ID NO: 1 and a reverse primer of SEQ ID NO: 2, a primer pair for AHT5 comprising a forward primer of SEQ ID NO: 3 and a reverse primer of SEQ ID NO: 4, a primer pair for ASB2 comprising a forward primer of SEQ ID NO: 5 and a reverse primer of SEQ ID NO: 6, a primer pair for HMS3 comprising a forward primer of SEQ ID NO: 7 and a reverse primer of SEQ ID NO: 8, a primer pair for HMS6 comprising a forward primer of SEQ ID NO: 9 and a reverse primer of SEQ ID NO: 10, a primer pair for HMS7 comprising a forward primer of SEQ ID NO: 11 and a reverse primer of SEQ ID NO: 12, a primer pair for HTG4 comprising a forward primer of SEQ ID NO: 13 and a reverse primer of SEQ ID NO: 14, a primer pair for HTG10 comprising a forward primer of SEQ ID NO: 15 and a reverse primer of SEQ ID NO: 16, a primer pair for VHL20 comprising a forward primer of SEQ ID NO: 17 and a reverse primer of SEQ ID NO: 18, a primer pair for ASB17 comprising a forward primer of SEQ ID NO: 19 and a reverse primer of SEQ ID NO: 20, a primer pair for ASB23 comprising a forward primer of SEQ ID NO:

21 and a reverse primer of SEQ ID NO: 22, a primer pair for HMS1 comprising a forward primer of SEQ ID NO: 23 and a reverse primer of SEQ ID NO: 24, a primer pair for LEX3 comprising a forward primer of SEQ ID NO: 25 and a reverse primer of SEQ ID NO: 26, a primer pair for CA425 comprising a forward primer of SEQ ID NO: 27 and a reverse primer of SEQ ID NO: 28, a primer pair for HMS2 comprising a forward primer of SEQ ID NO: 29 and a reverse primer of SEQ ID NO: 30, a primer pair for HTG6 comprising a forward primer of SEQ ID NO: 31 and a reverse primer of SEQ ID NO: 32, a primer pair for HTG7 comprising a forward primer of SEQ ID NO: 33 and a reverse primer of SEQ ID NO: 34, a primer pair for LEX033 comprising a forward primer of SEQ ID NO: 35 and a reverse primer of SEQ ID NO: 36, a primer pair for AMEL comprising a forward primer of SEQ ID NO: 37 and a reverse primer of SEQ ID NO: 38, a primer pair for HMS18 comprising a forward primer of SEQ ID NO: 39 and a reverse primer of SEQ ID NO: 40, a primer pair for LEX27 comprising a forward primer of SEQ ID NO: 41 and a reverse primer of SEQ ID NO: 42, a primer pair for SRY comprising a forward primer of SEQ ID NO: 43 and a reverse primer of SEQ ID NO: 44, and a primer pair for LEX020 comprising a forward primer of SEQ ID NO: 45 and a reverse primer of SEQ ID NO: 46; and a second primer set consisting of a primer pair for HTG21 comprising a forward primer of SEQ ID NO: 47 and a reverse primer of SEQ ID NO: 48, a primer pair for COR089 comprising a forward primer of SEQ ID NO: 49 and a reverse primer of SEQ ID NO: 50, a primer pair for TKY279 comprising a forward primer of SEQ ID NO: 51 and a reverse primer of SEQ ID NO: 52, a primer pair for TKY287 comprising a forward primer of SEQ ID NO: 53 and a reverse primer of SEQ ID NO: 54, a primer pair for TKY294 comprising a forward primer of SEQ ID NO: 55 and a reverse primer of SEQ ID NO: 56, a primer pair for TKY297 comprising a forward primer of SEQ ID NO: 57 and a reverse primer of SEQ ID NO: 58, a primer pair for TKY301 comprising a forward primer of SEQ ID NO: 59 and a reverse primer of SEQ ID NO: 60, a primer pair for TKY312 comprising a forward primer of SEQ ID NO: 61 and a reverse primer of SEQ ID NO: 62, a primer pair for TKY321 comprising a forward primer of SEQ ID NO: 63 and a reverse primer of SEQ ID NO: 64, a primer pair for TKY325 comprising a forward primer of SEQ ID NO: 65 and a reverse primer of SEQ ID NO: 66, a primer pair for TKY333 comprising a forward primer of SEQ ID NO: 67 and a reverse primer of SEQ ID NO: 68, a primer pair for TKY337 comprising a forward primer of SEQ ID NO: 69 and a reverse primer of SEQ ID NO: 70, a primer pair for TKY341 comprising a forward primer of SEQ ID NO: 71 and a reverse primer of SEQ ID NO: 72, a primer pair for TKY343 comprising a forward primer of SEQ ID NO: 73 and a reverse primer of SEQ ID NO: 74, a primer pair for TKY344 comprising a forward primer of SEQ ID NO: 75 and a reverse primer of SEQ ID NO: 76, a primer pair for TKY374 comprising a forward primer of SEQ ID NO: 77 and a reverse primer of SEQ ID NO: 78, and a primer pair for TKY394 comprising a forward primer of SEQ ID NO: 79 and a reverse primer of SEQ ID NO: 80, wherein the primers comprise SEQ ID NOS: 1 to 80; and detecting alleles in the product amplified in the multiplex PCR amplification step and analyzing the sizes of the alleles using an electrophoresis apparatus to determine a genotype of the racehorse.

2. The method of claim 1, wherein, in the multiplex PCR amplification step, the multiplex PCR amplification conditions include maintenance at 95° C. for 2 minutes, followed by repeating 33 cycles of denaturation at 95° C. for 30 seconds, annealing at 56.5° C. for 90 seconds and extension at 72° C. for 60 seconds, and the final extension at 72° C. for 30 minutes and maintenance at 4° C.

* * * * *

SEQUENCE LISTING

<160> NUMBER OF SEQ ID NOS: 80

<210> SEQ ID NO 1
<211> LENGTH: 20
<212> TYPE: DNA
<213> ORGANISM: Equus caballus

<400> SEQUENCE: 1
aaccgcctga gcaaggaagt          20

<210> SEQ ID NO 2
<211> LENGTH: 20
<212> TYPE: DNA
<213> ORGANISM: Equus caballus

<400> SEQUENCE: 2
gctcccagag agtttaccct          20

<210> SEQ ID NO 3
<211> LENGTH: 20
<212> TYPE: DNA
<213> ORGANISM: Equus caballus

<400> SEQUENCE: 3

```
acggacacat ccctgcctgc                                          20

<210> SEQ ID NO 4
<211> LENGTH: 20
<212> TYPE: DNA
<213> ORGANISM: Equus caballus

<400> SEQUENCE: 4
gcaggctaag ggggctcagc                                          20

<210> SEQ ID NO 5
<211> LENGTH: 23
<212> TYPE: DNA
<213> ORGANISM: Equus caballus

<400> SEQUENCE: 5
ccactaagtg tcgtttcaga agg                                      23

<210> SEQ ID NO 6
<211> LENGTH: 22
<212> TYPE: DNA
<213> ORGANISM: Equus caballus

<400> SEQUENCE: 6
cacaactgag ttctctgata gg                                       22

<210> SEQ ID NO 7
<211> LENGTH: 24
<212> TYPE: DNA
<213> ORGANISM: Equus caballus

<400> SEQUENCE: 7
ccatcctcac tttttcactt tgtt                                     24

<210> SEQ ID NO 8
<211> LENGTH: 24
<212> TYPE: DNA
<213> ORGANISM: Equus caballus

<400> SEQUENCE: 8
ccaactcttt gtcacataac aaga                                     24

<210> SEQ ID NO 9
<211> LENGTH: 24
<212> TYPE: DNA
<213> ORGANISM: Equus caballus

<400> SEQUENCE: 9
gaagctgcca gtattcaacc attg                                     24

<210> SEQ ID NO 10
<211> LENGTH: 24
<212> TYPE: DNA
<213> ORGANISM: Equus caballus

<400> SEQUENCE: 10
ctccatcttg tgaagtgtaa ctca                                     24

<210> SEQ ID NO 11
<211> LENGTH: 24
<212> TYPE: DNA
<213> ORGANISM: Equus caballus

<400> SEQUENCE: 11
```
caggaaactc atgttgatac catc                                              24

<210> SEQ ID NO 12
<211> LENGTH: 25
<212> TYPE: DNA
<213> ORGANISM: Equus caballus

<400> SEQUENCE: 12
tgttgttgaa atacccttg actgt                                              25

<210> SEQ ID NO 13
<211> LENGTH: 24
<212> TYPE: DNA
<213> ORGANISM: Equus caballus

<400> SEQUENCE: 13
ctatctcagt cttgattgca ggac                                              24

<210> SEQ ID NO 14
<211> LENGTH: 22
<212> TYPE: DNA
<213> ORGANISM: Equus caballus

<400> SEQUENCE: 14
ctccctccct ccctctgttc tc                                                22

<210> SEQ ID NO 15
<211> LENGTH: 24
<212> TYPE: DNA
<213> ORGANISM: Equus caballus

<400> SEQUENCE: 15
tttttattct gatctgtcac attt                                              24

<210> SEQ ID NO 16
<211> LENGTH: 23
<212> TYPE: DNA
<213> ORGANISM: Equus caballus

<400> SEQUENCE: 16
caattcccgc cccaccccg gca                                                23

<210> SEQ ID NO 17
<211> LENGTH: 24
<212> TYPE: DNA
<213> ORGANISM: Equus caballus

<400> SEQUENCE: 17
caagtcctct tacttgaaga ctag                                              24

<210> SEQ ID NO 18
<211> LENGTH: 23
<212> TYPE: DNA
<213> ORGANISM: Equus caballus

<400> SEQUENCE: 18
aactcaggga gaatcttcct cag                                               23

<210> SEQ ID NO 19
<211> LENGTH: 20
<212> TYPE: DNA
<213> ORGANISM: Equus caballus

<400> SEQUENCE: 19
gagggcggta cctttgtacc                                              20

<210> SEQ ID NO 20
<211> LENGTH: 20
<212> TYPE: DNA
<213> ORGANISM: Equus caballus

<400> SEQUENCE: 20
accattcagg atctccaccg                                              20

<210> SEQ ID NO 21
<211> LENGTH: 21
<212> TYPE: DNA
<213> ORGANISM: Equus caballus

<400> SEQUENCE: 21
gagggcagca ggttgggaag g                                            21

<210> SEQ ID NO 22
<211> LENGTH: 23
<212> TYPE: DNA
<213> ORGANISM: Equus caballus

<400> SEQUENCE: 22
acatcctggt caaatcacag tcc                                          23

<210> SEQ ID NO 23
<211> LENGTH: 23
<212> TYPE: DNA
<213> ORGANISM: Equus caballus

<400> SEQUENCE: 23
catcactctt catgtctgct tgg                                          23

<210> SEQ ID NO 24
<211> LENGTH: 25
<212> TYPE: DNA
<213> ORGANISM: Equus caballus

<400> SEQUENCE: 24
ttgacataaa tgcttatcct atggc                                        25

<210> SEQ ID NO 25
<211> LENGTH: 22
<212> TYPE: DNA
<213> ORGANISM: Equus caballus

<400> SEQUENCE: 25
acatctaacc agtgctgaga ct                                           22

<210> SEQ ID NO 26
<211> LENGTH: 23
<212> TYPE: DNA
<213> ORGANISM: Equus caballus

<400> SEQUENCE: 26
gaaggaaaaa aaaggaggaa gac                                          23

<210> SEQ ID NO 27
<211> LENGTH: 18
<212> TYPE: DNA
<213> ORGANISM: Equus caballus

```
<400> SEQUENCE: 27
agctgcctcg ttaattca                                              18

<210> SEQ ID NO 28
<211> LENGTH: 18
<212> TYPE: DNA
<213> ORGANISM: Equus caballus

<400> SEQUENCE: 28
ctcatgtccg cttgtctc                                              18

<210> SEQ ID NO 29
<211> LENGTH: 25
<212> TYPE: DNA
<213> ORGANISM: Equus caballus

<400> SEQUENCE: 29
cttgcagtcg aatgtgtatt aaatg                                      25

<210> SEQ ID NO 30
<211> LENGTH: 22
<212> TYPE: DNA
<213> ORGANISM: Equus caballus

<400> SEQUENCE: 30
acggtggcaa ctgccaagga ag                                         22

<210> SEQ ID NO 31
<211> LENGTH: 24
<212> TYPE: DNA
<213> ORGANISM: Equus caballus

<400> SEQUENCE: 31
cctgcttgga ggctgtgata agat                                       24

<210> SEQ ID NO 32
<211> LENGTH: 24
<212> TYPE: DNA
<213> ORGANISM: Equus caballus

<400> SEQUENCE: 32
gttcactgaa tgtcaaattc tgct                                       24

<210> SEQ ID NO 33
<211> LENGTH: 24
<212> TYPE: DNA
<213> ORGANISM: Equus caballus

<400> SEQUENCE: 33
cctgaagcag aacatccctc cttg                                       24

<210> SEQ ID NO 34
<211> LENGTH: 24
<212> TYPE: DNA
<213> ORGANISM: Equus caballus

<400> SEQUENCE: 34
ataaagtgtc tgggcagagc tgct                                       24

<210> SEQ ID NO 35
<211> LENGTH: 21
<212> TYPE: DNA
```

<213> ORGANISM: Equus caballus

<400> SEQUENCE: 35
tttaatcaaa ggattcagtt g					21

<210> SEQ ID NO 36
<211> LENGTH: 20
<212> TYPE: DNA
<213> ORGANISM: Equus caballus

<400> SEQUENCE: 36
gggacacttt ctttactttc					20

<210> SEQ ID NO 37
<211> LENGTH: 26
<212> TYPE: DNA
<213> ORGANISM: Equus caballus

<400> SEQUENCE: 37
cacttcctgg ccaacactcc atggtt				26

<210> SEQ ID NO 38
<211> LENGTH: 26
<212> TYPE: DNA
<213> ORGANISM: Equus caballus

<400> SEQUENCE: 38
gccaagcttc cagaggcagg tcagga				26

<210> SEQ ID NO 39
<211> LENGTH: 24
<212> TYPE: DNA
<213> ORGANISM: Equus caballus

<400> SEQUENCE: 39
caacaatgaa aatttgtcct gtgc				24

<210> SEQ ID NO 40
<211> LENGTH: 24
<212> TYPE: DNA
<213> ORGANISM: Equus caballus

<400> SEQUENCE: 40
gtaaatgagt agacaatcat gagg				24

<210> SEQ ID NO 41
<211> LENGTH: 20
<212> TYPE: DNA
<213> ORGANISM: Equus caballus

<400> SEQUENCE: 41
accactggga aactgtgtaa					20

<210> SEQ ID NO 42
<211> LENGTH: 16
<212> TYPE: DNA
<213> ORGANISM: Equus caballus

<400> SEQUENCE: 42
gcccagaatc cgaacc					16

<210> SEQ ID NO 43
<211> LENGTH: 29

<212> TYPE: DNA
<213> ORGANISM: Equus caballus

<400> SEQUENCE: 43
cttaagcttc tgctatgtcc agagtatcc                                29

<210> SEQ ID NO 44
<211> LENGTH: 28
<212> TYPE: DNA
<213> ORGANISM: Equus caballus

<400> SEQUENCE: 44
gcggtttgtc acttttctgt ggcatctt                                 28

<210> SEQ ID NO 45
<211> LENGTH: 20
<212> TYPE: DNA
<213> ORGANISM: Equus caballus

<400> SEQUENCE: 45
ggaataggtg ggggtctgtt                                          20

<210> SEQ ID NO 46
<211> LENGTH: 22
<212> TYPE: DNA
<213> ORGANISM: Equus caballus

<400> SEQUENCE: 46
agggtactag ccaagtgact gc                                       22

<210> SEQ ID NO 47
<211> LENGTH: 23
<212> TYPE: DNA
<213> ORGANISM: Equus caballus

<400> SEQUENCE: 47
attacttcct ccaggtatct cag                                      23

<210> SEQ ID NO 48
<211> LENGTH: 19
<212> TYPE: DNA
<213> ORGANISM: Equus caballus

<400> SEQUENCE: 48
aggcagggct gggagacgt                                           19

<210> SEQ ID NO 49
<211> LENGTH: 20
<212> TYPE: DNA
<213> ORGANISM: Equus caballus

<400> SEQUENCE: 49
cctgccataa atttgtttcc                                          20

<210> SEQ ID NO 50
<211> LENGTH: 20
<212> TYPE: DNA
<213> ORGANISM: Equus caballus

<400> SEQUENCE: 50
tccctacctc atctccacac                                          20

<210> SEQ ID NO 51

-continued

```
<210> SEQ ID NO 51
<211> LENGTH: 19
<212> TYPE: DNA
<213> ORGANISM: Equus caballus

<400> SEQUENCE: 51
aatgaatgag acttgaacc                                                   19

<210> SEQ ID NO 52
<211> LENGTH: 19
<212> TYPE: DNA
<213> ORGANISM: Equus caballus

<400> SEQUENCE: 52
tctgctgttt taggctcgg                                                   19

<210> SEQ ID NO 53
<211> LENGTH: 20
<212> TYPE: DNA
<213> ORGANISM: Equus caballus

<400> SEQUENCE: 53
atcagagaac accaagaagg                                                  20

<210> SEQ ID NO 54
<211> LENGTH: 20
<212> TYPE: DNA
<213> ORGANISM: Equus caballus

<400> SEQUENCE: 54
tctctgctat aggtaaggtc                                                  20

<210> SEQ ID NO 55
<211> LENGTH: 21
<212> TYPE: DNA
<213> ORGANISM: Equus caballus

<400> SEQUENCE: 55
gatctatgtg ctagcaaaca c                                                21

<210> SEQ ID NO 56
<211> LENGTH: 20
<212> TYPE: DNA
<213> ORGANISM: Equus caballus

<400> SEQUENCE: 56
ctagtgtttc agatagcctc                                                  20

<210> SEQ ID NO 57
<211> LENGTH: 20
<212> TYPE: DNA
<213> ORGANISM: Equus caballus

<400> SEQUENCE: 57
gtctttttgt gcctctggtg                                                  20

<210> SEQ ID NO 58
<211> LENGTH: 20
<212> TYPE: DNA
<213> ORGANISM: Equus caballus

<400> SEQUENCE: 58 tcagggggaca gtggcagcag                                                 20
```

```
<210> SEQ ID NO 59
<211> LENGTH: 20
<212> TYPE: DNA
<213> ORGANISM: Equus caballus

<400> SEQUENCE: 59
aatggtggct aatcaatggg                                               20

<210> SEQ ID NO 60
<211> LENGTH: 20
<212> TYPE: DNA
<213> ORGANISM: Equus caballus

<400> SEQUENCE: 60
gtgtatgatg ccctcatctc                                               20

<210> SEQ ID NO 61
<211> LENGTH: 20
<212> TYPE: DNA
<213> ORGANISM: Equus caballus

<400> SEQUENCE: 61
aacctgggtt tctgttgttg                                               20

<210> SEQ ID NO 62
<211> LENGTH: 20
<212> TYPE: DNA
<213> ORGANISM: Equus caballus

<400> SEQUENCE: 62
gatccttctt tttatggctg                                               20

<210> SEQ ID NO 63
<211> LENGTH: 22
<212> TYPE: DNA
<213> ORGANISM: Equus caballus

<400> SEQUENCE: 63
ttgttgggtt taggtatgaa gg                                            22

<210> SEQ ID NO 64
<211> LENGTH: 22
<212> TYPE: DNA
<213> ORGANISM: Equus caballus

<400> SEQUENCE: 64
gtgtcaatgt gacttcaaga ac                                            22

<210> SEQ ID NO 65
<211> LENGTH: 20
<212> TYPE: DNA
<213> ORGANISM: Equus caballus

<400> SEQUENCE: 65
ggatggagtg agataatacc                                               20

<210> SEQ ID NO 66
<211> LENGTH: 20
<212> TYPE: DNA
<213> ORGANISM: Equus caballus

<400> SEQUENCE: 66
tggatgaacc atgaatagtg                                               20
```

```
<210> SEQ ID NO 67
<211> LENGTH: 20
<212> TYPE: DNA
<213> ORGANISM: Equus caballus

<400> SEQUENCE: 67
ccttcactag ccttcaaatg                                              20

<210> SEQ ID NO 68
<211> LENGTH: 20
<212> TYPE: DNA
<213> ORGANISM: Equus caballus

<400> SEQUENCE: 68
ttgtgtttag acagtgctgc                                              20

<210> SEQ ID NO 69
<211> LENGTH: 20
<212> TYPE: DNA
<213> ORGANISM: Equus caballus

<400> SEQUENCE: 69
agcagggttt aattaccgag                                              20

<210> SEQ ID NO 70
<211> LENGTH: 20
<212> TYPE: DNA
<213> ORGANISM: Equus caballus

<400> SEQUENCE: 70
tagatgctaa tgcagcacag                                              20

<210> SEQ ID NO 71
<211> LENGTH: 20
<212> TYPE: DNA
<213> ORGANISM: Equus caballus

<400> SEQUENCE: 71
tatccagtca cccattttac                                              20

<210> SEQ ID NO 72
<211> LENGTH: 20
<212> TYPE: DNA
<213> ORGANISM: Equus caballus

<400> SEQUENCE: 72
ttgtgtcagt acactctatg                                              20

<210> SEQ ID NO 73
<211> LENGTH: 20
<212> TYPE: DNA
<213> ORGANISM: Equus caballus

<400> SEQUENCE: 73
tagtccctat ttctcctgag                                              20

<210> SEQ ID NO 74
<211> LENGTH: 20
<212> TYPE: DNA
<213> ORGANISM: Equus caballus

<400> SEQUENCE: 74
aaacccacag atactctaga                                              20
```

```
<210> SEQ ID NO 75
<211> LENGTH: 20
<212> TYPE: DNA
<213> ORGANISM: Equus caballus

<400> SEQUENCE: 75
gtgtccatca atggatgaag                                          20

<210> SEQ ID NO 76
<211> LENGTH: 21
<212> TYPE: DNA
<213> ORGANISM: Equus caballus

<400> SEQUENCE: 76
cttaaggcta aataatatcc c                                        21

<210> SEQ ID NO 77
<211> LENGTH: 20
<212> TYPE: DNA
<213> ORGANISM: Equus caballus

<400> SEQUENCE: 77
ctggtccctc tggatggaag                                          20

<210> SEQ ID NO 78
<211> LENGTH: 20
<212> TYPE: DNA
<213> ORGANISM: Equus caballus

<400> SEQUENCE: 78
tcccaagagg gagtacaatc                                          20

<210> SEQ ID NO 79
<211> LENGTH: 20
<212> TYPE: DNA
<213> ORGANISM: Equus caballus

<400> SEQUENCE: 79
gcatcatcgc cttgaagttg                                          20

<210> SEQ ID NO 80
<211> LENGTH: 20
<212> TYPE: DNA
<213> ORGANISM: Equus caballus

<400> SEQUENCE: 80
cctttctggt tggtatcctg                                          20
```